US00PP31876P2

(12) United States Plant Patent
Horvath

(10) Patent No.: US PP31,876 P2
(45) Date of Patent: Jun. 16, 2020

(54) ***PRUNELLA VULGARIS* PLANT NAMED 'MAGDALENA'**

(50) Latin Name: *Prunella vulgaris*
Varietal Denomination: Magdalena

(71) Applicant: Brent Horvath, Fontana, WI (US)

(72) Inventor: Brent Horvath, Fontana, WI (US)

( * ) Notice: Subject to any disclaimer, the term of this patent is extended or adjusted under 35 U.S.C. 154(b) by 0 days.

(21) Appl. No.: 16/350,747

(22) Filed: Jan. 2, 2019

(51) Int. Cl.
*A01H 5/02* (2018.01)
*A01H 6/50* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
*Assistant Examiner* — Karen M Redden

(57) ABSTRACT

A new, distinct *Prunella vulgaris* plant as shown and described, characterized by the combination of large purple flowers, tall habit and reblooms.

1 Drawing Sheet

Figure 1:
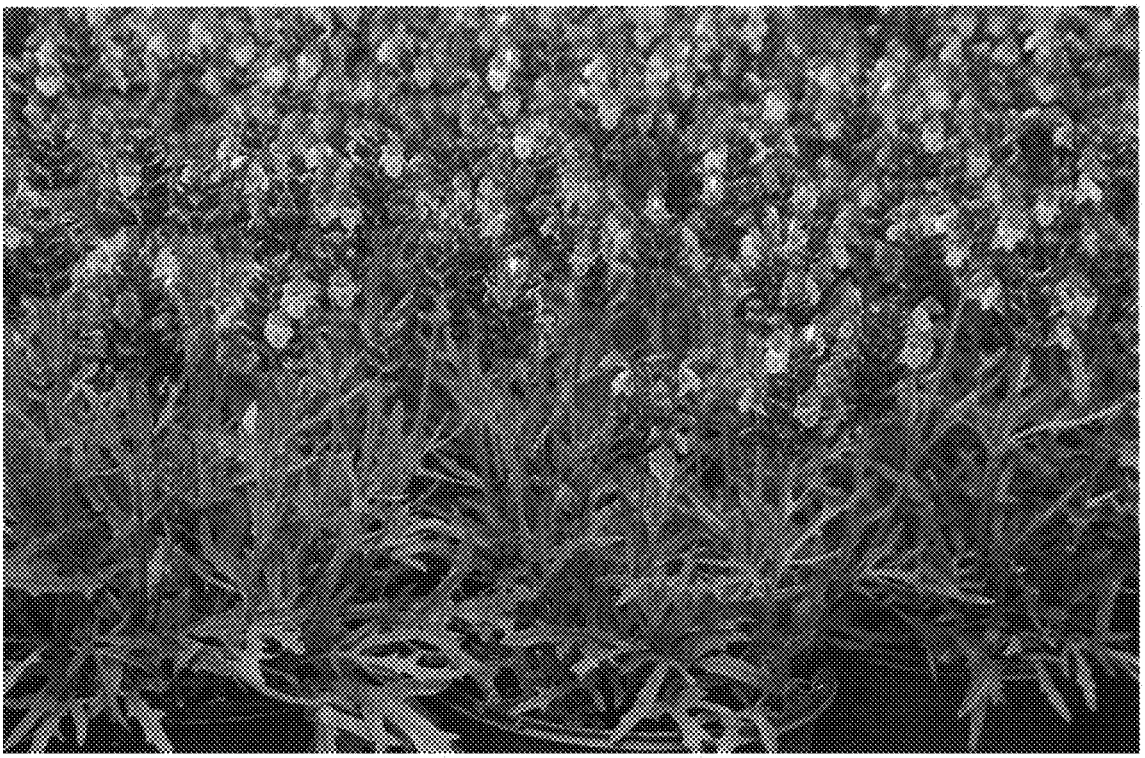

Latin name: *Prunella vulgaris*.
Cultivar name: 'Magdalena'.

BACKGROUND OF THE INVENTION

The present invention relates to a new and distinct hybrid of *Prunella vulgaris* plant named 'Magdalena' characterized by the combination of larger purple flowers, taller habit and rebloom compared to the seed parent. The new *Prunella vulgaris* was raised as a seedling from open pollinated seed sown from the seed parent, *Prunella vulgaris* 'Under the Sea', not patented, in Hebron, Ill. in 2014. The selection of the new plant was due to its' larger purple flowers, taller habit and rebloom, compared to the seed parent. Initial asexual reproduction has taken place at a nursery in Hebron, Ill. since 2015 by means of division, and vegetative cuttings. The new *Prunella vulgaris* has shown to be stable and identical in reproduction to the originally discovered plant after rooting over 1000 plants from 2015 to 2018. No plants of the new *Prunella vulgaris* have been sold in this country, or anywhere in the world, prior to the filing of this application, nor has any disclosure of the new plant been made prior to the filing of this application with the exception of that which was disclosed within one year of filing of this application and was either derived directly or indirectly for the inventor.

SUMMARY OF THE INVENTION

The new *Prunella vulgaris* plant named 'Magdalena', characterized larger purple flowers, taller habit and rebloom, compared to the seed parent have been observed to be unique and stable. For purpose of comparison the new plant will be referred to as 'Magdalena'.

Plants of 'Magdalena' can be compared to the seed parent plant of *Prunella vulgaris* 'Under the Sea', not patented. 1. The 'Magdalena' plant is taller growing to 26 cm while *Prunella vulgaris* 'Under the Sea', grows to 20 cm. 2. The 'Magdalena' plant has a larger purple flower color of 86 A aging to 91 D, while *Prunella vulgaris* 'Under the Sea', has a flower color of lilac purple.

Plants of 'Magdalena' can be compared to the plant of *Prunella vulgaris* 'Summer Daze' U.S. Pat. No. 19,609, patented. 1. The 'Magdalena' plant has a purple flower 86 A aging to 91 D, while *Prunella vulgaris* 'Summer Daze' has a flower color of 73 A aging to N74 B.

DESCRIPTION OF PHOTOGRAPHS

Plants pictured in the drawing were grown for one year in a 1 gallon pot.

FIG. 1. Close up of the flowering plant in June.

Figure 2:
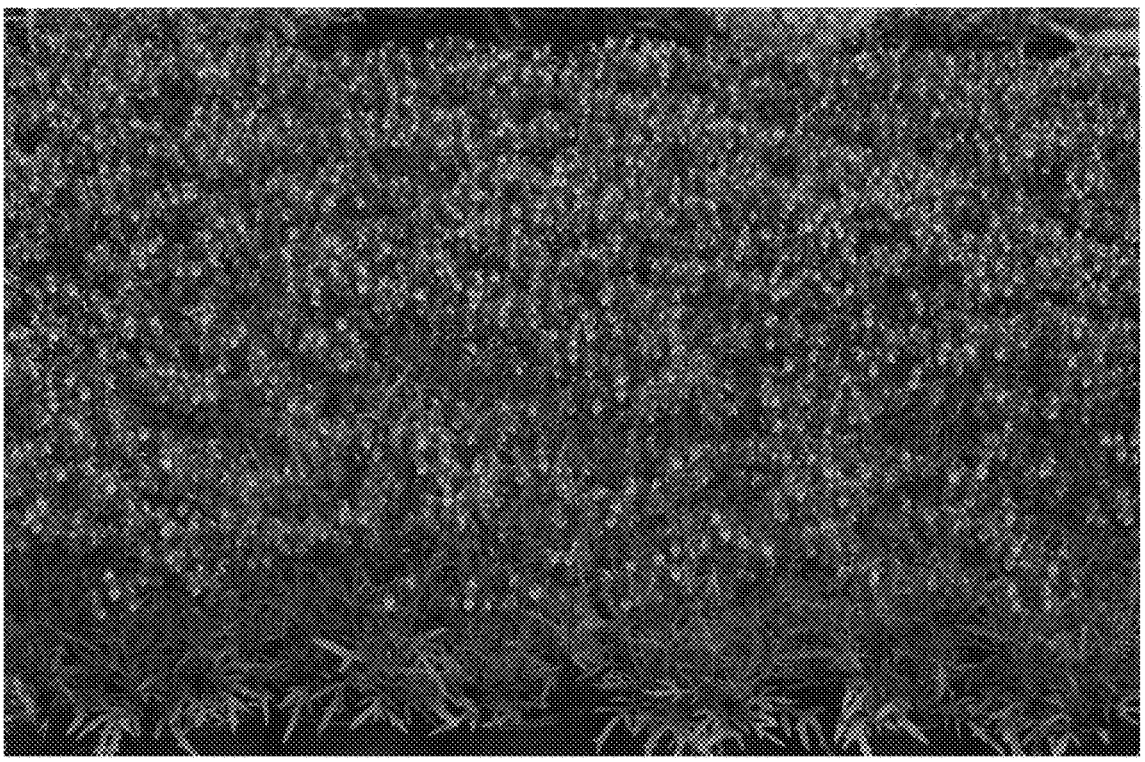

FIG. 2. A group of potted plants flowering in June.

DETAILED BOTANICAL DESCRIPTION

In the following description, color references are made to The Royal Horticultural Society Colour Chart (2001). Plants used for the description were grown for one year. Measurements and numerical values represent averages of typical plants.

Plant:

*Botanical classification.*—*Prunella vulgaris.*
*Parentage.*—Female: *Prunella vulgaris* 'Under the Sea'; Male: An unknown, *Prunella vulgaris.*
*Habit.*—Dense, matting.
*Height.*—26 cm from soil to top of flowers; 30 cm wide.
*Growth.*—Herbaceous perennial, broad upright, vigorous.
*Roots.*—Fine, compact, dense, freely branching, white.

Foliage:

*Arrangement.*—Opposite.
*Size of leaf.*—Length: 10 cm, Width: 5 cm.
*Shape of leaf.*—Lyrate.
*Shape of tip.*—Rounded.
*Shape of base.*—Obique.
*Texture.*—Puberulent.
*Margin type.*—Pinnatilobate.
*Color.*—Young and Mature leaves: Upper surface: 137 B. Lower surface: close to 146 B.
*Petioles.*—Length: Up to 30 mm. Diameter: 3 mm, Color: 146 C. Shape: Sulcate.

*Texture*.—Villous.
*Veins*.—Pattern: Pinnate. Color: Upper surface: 137 B. Lower surface: 146 C.
*Durability*.—Highly durable to stresses; when crushed, foliage has no odor.
*Response time to flower*.—About 10 months when grown in the containers.

Flower:
*Natural flowering season*.—Continuous from June into July with some rebloom July and August.
*Inflorescence type and habit*.—Verticillaster, labiate, no fragrance, flower lasts about three weeks on plant, self-cleaning.
*Rate of flower opening*.—About 50-75% of flowers open at once, all flowers open in about 4 weeks.
*Number of flowers*.—About 30 per spike; about 20 stems, 600 flowers per plant.
*Inflorescence size*.—Length: 55 mm. Width: 45 mm.
*Shape*.—Deltoid.
*Quantity*.—About 20 flowering lateral stems.
*Peduncle*.—
*Shape*.—Quadrilateral.
*Surface*.—Lanate.
*Color*.—146 C.
*Orientation*.—Upright.
*Strength*.—Strong.
*Bract*.—
*Quantity*.—2 at the base of the peduncle.
*Shape*.—Hastate.
*Surface*.—Upper and lower: Villous.
*Bract size*.—Length: 11 mm. Width: 10 mm.
*Apex*.—Acute.
*Base*.—Attenuate.
*Margin*.—Entire.
*Color*.—145 C at the base, tips and veins 141 B.
*Aspect*.—Outward and upright.
*Corolla*.—
*Petal arrangement*.—Labiate with one upper lip and one lower lip having one main lobe and two smaller side lobes.
*Overall size*.—25 mm in length; 10 mm in depth. Corolla tube dimensions 25 mm in length and 2 mm in diameter.
*Margin*.—Entire upper lip; 3-lobed lower lip.
*Lip shape*.—Hooded upper lip; rounded lower lip.
*Petal quantity*.—2, fused at base.
*Petal apex shape*.—Upper lip; Hooded, obtuse; lower lip tri-lobed and deflexed.
*Texture*.—Glabrous.
*Aspect*.—Drooping.
*Color*.—When opening and fully open: Upper and lower surface: Upper Lip: 86 A. Upper and lower surface: Lower Lip: 91 D.
*Bud*.—
*Shape*.—Ovate.
*Bud apex*.—Obtuse.
*Surface*.—Puberulent.
*Bud size*.—Height: 10 mm. Width: 4 mm.
*Color*.—N89 A.
*Calyx*.—
*Shape*.—Tubular.
*Surfaces*.—Upper and lower: Villous.
*Color*.—Partially green on the base, Adaxial portion 146 D, becoming N77 A at flowering and after flowers drop.
*Arrangement*.—Fused.
*Calyx size*.—Height: 10 mm. Width: 4 mm.
*Sepals*.—Shape: Apex: Acute. Base: crenate. Size: Average 7 mm long; 1-2 mm wide.
*Margin*.—Entire.
*Texture*.—Villous; less than 0.5 mm long.
*Color*.—Outer surface: 141 B, at the base: 145 C.
*Odor*.—Not present in petals and sepals.

Reproductive organs:
*Stamens*.—
*Color*.—76 C.
*Number*.—4.
*Filament length*.—16 mm.
*Anthers*.—Shape: Basifixed, elliptic. Length: 0.5 mm. Color: 76 C.
*Pollen*.—Color: White, close to N155 D. Amount: Very low.
*Pistil*.—
*Number*.—1.
*Length*.—12 mm.
*Shape*.—Filiform.
*Color*.—76 D.
*Style*.—Length: 24 mm. Color: N155 A at the top half fading to white at the base.
*Stigma*.—Shape: Bifid. Color: 76 D.
*Ovary*.—Position: Inferior. Shape: Ovate. Height: 1 mm. Width 1 mm. Color: 145 C.
*Seeds and fruits*.—Brown, color 200 B, and round 0.05 mm long and 1 mm wide.
*Disease/pest resistance*.—No unusual susceptibility to diseases or pests has been noted to date.
*Temperature tolerance*.—Tolerate to heat at least up to 30° C. and cool at least down to −28.9° C. USDA Zone 5.

I claim:

1. A new, distinct *Prunella vulgaris* plant as shown and described, characterized by the combination of larger purple flowers, taller habit and rebloom compared to the seed parent.

* * * * *